(12) United States Patent
Boettcher et al.

(10) Patent No.: US 10,004,445 B2
(45) Date of Patent: Jun. 26, 2018

(54) APPARATUS AND METHOD FOR STIMULATOR ON-SKIN SHORT DETECTION

(71) Applicant: Neurometrix, Inc., Waltham, MA (US)

(72) Inventors: Bonniejean Boettcher, Maynard, MA (US); Glenn Herb, Weston, MA (US); Xuan Kong, Acton, MA (US)

(73) Assignee: NeuroMetrix, Inc., Waltham, MA (US)

( * ) Notice: Subject to any disclaimer, the term of this patent is extended or adjusted under 35 U.S.C. 154(b) by 859 days.

(21) Appl. No.: 14/505,056

(22) Filed: Oct. 2, 2014

(65) Prior Publication Data

US 2015/0038873 A1  Feb. 5, 2015

Related U.S. Application Data

(63) Continuation-in-part of application No. 13/235,258, filed on Sep. 16, 2011, now Pat. No. 9,173,581.
(Continued)

(51) Int. Cl.
*A61B 5/05* (2006.01)
*A61B 5/00* (2006.01)
(Continued)

(52) U.S. Cl.
CPC ........ *A61B 5/4041* (2013.01); *A61B 5/04001* (2013.01); *A61B 5/05* (2013.01);
(Continued)

(58) Field of Classification Search
CPC . A61B 5/04001; A61B 5/4029; A61B 5/4041; A61B 5/4047; A61B 5/4052; A61B 5/4893; A61B 5/6828; A61B 2560/0276
See application file for complete search history.

(56) References Cited

U.S. PATENT DOCUMENTS

| 2,327,874 A | 8/1943 | Jong |
| D243,417 S | 2/1977 | Allen et al. |

(Continued)

FOREIGN PATENT DOCUMENTS

| JP | S60-41851 | 3/1985 |
| JP | S60-194933 | 10/1985 |
| WO | WO 00/09999 | 2/2000 |
| WO | WO 2012/037527 | 3/2012 |

OTHER PUBLICATIONS

Albers et al., Subclinical Neuropathy Among Diabetes Control And Complications Trial Participants Without Diagnosable Neuropathy At Trial Completion, Diabetes Care, Oct. 2007, pp. 2613-2618.
(Continued)

*Primary Examiner* — Lee S Cohen
*Assistant Examiner* — Erin M Cardinal
(74) *Attorney, Agent, or Firm* — Pandiscio & Pandiscio

(57) ABSTRACT

The invention relates to apparatus and methods for stimulating living tissues to determine nerve conduction properties using a pair of stimulator probes and a plurality of detection electrodes. The invention overcomes the problem of reporting potentially inaccurate nerve conduction results by detecting a stimulator probe short or shunt condition during nerve conduction tests. Detection of a short or shunt condition between two stimulator probes is accomplished by monitoring the magnitude of the stimulus artifact waveform acquired from the detection electrodes and the voltage difference between the stimulator probes. A test is flagged when magnitude of the stimulus artifact waveform is below a first threshold and voltage difference between the two stimulator probes is below a second threshold. The first and second threshold values are determined based on the known spatial relationship between the stimulator probes and detection electrodes. Feedback is provided to the tester to alert defective test conditions.

8 Claims, 12 Drawing Sheets

Related U.S. Application Data

(60) Provisional application No. 61/403,453, filed on Sep. 16, 2010, provisional application No. 61/459,127, filed on Dec. 6, 2010, provisional application No. 61/467,857, filed on Mar. 25, 2011, provisional application No. 61/516,944, filed on Apr. 11, 2011, provisional application No. 61/571,203, filed on Jun. 22, 2011, provisional application No. 61/885,673, filed on Oct. 2, 2013.

(51) Int. Cl.
*A61B 5/04* (2006.01)
*A61B 5/01* (2006.01)

(52) U.S. Cl.
CPC .............. *A61B 5/6828* (2013.01); *A61B 5/01* (2013.01); *A61B 2560/0425* (2013.01); *A61B 2560/0468* (2013.01); *A61B 2562/0209* (2013.01); *A61B 2562/046* (2013.01)

(56) References Cited

U.S. PATENT DOCUMENTS

| | | |
|---|---|---|
| 4,033,356 A | 7/1977 | Hasa |
| 4,121,573 A | 10/1978 | Crovella et al. |
| D255,938 S | 7/1980 | Hawke et al. |
| 4,419,998 A | 12/1983 | Heath |
| D299,746 S | 2/1989 | Guldalian, Jr. |
| 5,215,100 A | 6/1993 | Spitz et al. |
| 5,327,902 A | 7/1994 | Lemmen |
| 5,755,750 A | 5/1998 | Petruska et al. |
| 5,806,522 A * | 9/1998 | Katims ............... A61B 5/4824 600/554 |
| 5,851,191 A | 12/1998 | Gozani |
| 5,991,355 A | 11/1999 | Dahlke |
| 6,132,386 A * | 10/2000 | Gozani ............... A61B 5/04004 600/554 |
| 6,146,335 A * | 11/2000 | Gozani ............... A61B 5/0488 600/554 |
| 6,298,255 B1 * | 10/2001 | Cordero ............ A61B 5/04085 600/372 |
| 6,312,392 B1 | 11/2001 | Herzon |
| 7,459,984 B2 | 12/2008 | Wang et al. |
| 7,760,428 B2 | 7/2010 | Sieckmann |
| 7,844,325 B2 | 11/2010 | Takehara |
| 7,917,201 B2 | 3/2011 | Gozani et al. |
| D638,131 S | 5/2011 | Buckels et al. |
| 8,948,876 B2 | 2/2015 | Gozani et al. |
| 9,173,581 B2 | 11/2015 | Boettcher et al. |
| 2002/0173828 A1 | 11/2002 | Gozani et al. |
| 2003/0093006 A1 | 5/2003 | Wells et al. |
| 2004/0231772 A1 | 11/2004 | Leonard et al. |
| 2005/0083527 A1 | 4/2005 | Flaherty et al. |
| 2006/0020291 A1 | 1/2006 | Gozani et al. |
| 2007/0129771 A1 | 6/2007 | Kurtz et al. |
| 2007/0149892 A1 | 6/2007 | Guldalian |
| 2007/0185409 A1 | 8/2007 | Wu et al. |
| 2007/0219441 A1 | 9/2007 | Carlin et al. |
| 2008/0288026 A1 | 11/2008 | Cross et al. |
| 2008/0306400 A1 | 12/2008 | Takehara |
| 2008/0312551 A1 * | 12/2008 | Fadem ............... A61B 5/04001 600/554 |
| 2012/0016259 A1 * | 1/2012 | Odderson .......... A61B 5/04001 600/554 |
| 2012/0226186 A1 | 9/2012 | Bears et al. |
| 2015/0174402 A1 | 6/2015 | Thomas et al. |

OTHER PUBLICATIONS

Behse et al., Sensory Action Potentials And Biopsy Of The Sural Nerve In Neuropathy, Brain, 1978, pp. 473-493.

Behse et al., Nerve Biopsy And Conduction Studies In Diabetic Neuropathy, Journal of Neurology, Neurosurgery, And Psychiatry, 1977, pp. 1072-1082.

Benatar et al., Reference Data For Commonly Used Sensory And Motor Nerve Conduction Studies, Muscle & Nerve, Nov. 2009, pp. 772-794.

Boettcher, Bonniejean et al., A Rapid, Low-cost, Point-of-care Test for Diabetic Peripheral Neuropathy, Jun. 24, 2011.

Boulton et al., Diabetic Neuropathies, Diabetes Care, Apr. 2005, pp. 956-962.

Burke et al., Sensory Conduction Of The Sural News In Polyneuropathy, Journal of Neurology, Neurosurgery, And Psychiatry, 1974, pp. 647-652.

Buschbacher, Sural And Saphenous 14-cm Antidromic Sensory Nerve Conduction Studies, Americal Journal of Physical Medicine & Rehabilitation, 2003, 82:421-426.

Charles et al., Low Peripheral Nerve Conduction Velocities And Amplitudes Are Strongly Related To Diabetic Microvascular Complications In Type 1 Diabetes, Diabetes Care, Dec. 2010, pp. 2648-2653.

Dros et al., Accuracy of Monofilament Testing to Diagnose Peripheral Neuropathy: A Systematic Review, Annals Of Family Medicine, Nov./Dec. 2009, pp. 555-558.

Dyck et al., Clinical And Neuropathological Criteria For The Diagnosis And Staging Of Diabetic Polyneuropathy, Brain, 1985, pp. 861-880.

Dyck et al., Fiber Loss Is Primary And Multifocal In Sural Nerves In Diabetic Polyneuropathy, Annals of Neurology, May 1986, pp. 425-439.

Dyck et al., Signs And Symptoms Versus Nerve Conduction Studies To Diagnose Diabetic Sensorimotor Polyneuropathy: CI Vs. NPhys Trial, Muscle & Nerve, Aug. 2010, pp. 157-164.

England et al., Distal Symmetrical Polyneuropathy: A Definition For Clinical Research, Neurology, Jan. 2005, pp. 199-207.

Esper et al., Sural And Radial Sensory Responses In Healthy Adults: Diagnostic Implications For Polyneuropathy, Muscle & Nerve, May 2005, pp. 628-632.

Gibbons et al., Diabetic Neuropathy, A Cross-Sectional Study Of The Relationship Among Tests Of Neurophysiology, Diabetes Care, Dec. 2010, pp. 2629-2634.

Gordois et al., The Health Care Costs of Diabetic Peripheral Neuropathy in the U.S., Diabetes Care, Jun. 2003, pp. 1790-1795.

Harrison et al., The Neuropathic Factor In The Aetiology Of Diabetic Foot Ulcers, Journal Of The Neurological Science, 1976, pp. 217-223.

Herman et al., Underdiagnosis Of Peripheral Neuropathy In Type 2 Diabetes, Diabetes Care, Jun. 2005, pp. 1480-1481.

Kihara et al., Comparison Of Electrophysiologic And Autonomic Tests In Sensory Diabetic Neuropathy, Clinical Autonomic Research, Aug. 1998, pp. 213-220.

Kirkman et al., Impact Of A Program To Improve Adherence To Diabetes Guidelines By Primary Care Physicians, Diabetes Care, Nov. 2002, pp. 1946-1951.

Kiziltan et al., Peripheral Neuropathy In Patients With Diabetic Foot Ulcers: Clinical And Nerve Conduction Study, Journal Of The Neurological Sciences, 2007, pp. 75-79.

Kong et al., Utilization Of Nerve Conduction Studies For The Diagnosis Of Polyneuropathy In Patients With Diabetes: A Retrospective Analysis Of A Large Patient Series, Journal of Diabetes Science and Technology, Mar. 2008, pp. 268-274.

Kong, Xuan et al., Repeatability of nerve conduction measurements derived entirely by computer methods, BioMedical Engineering OnLine, 2009, 8:33.

National Diabetes Fact Sheet, Department Of Health And Human Services, Centers for Disease Control And Prevention, 2007.

Pambianco et al., Risk Factor Associations With Clinical Distal Symmetrical Polyneuropathy And Various Neuropathy Screening Instruments And Protocols In Type 1 Diabetes, Diabetes Research And Clinical Practice, 2011, pp. e15-e20.

Pambianco et al., The Assessment Of Clinical Distal Symmetric Polyneuropathy in Type 1 Diabetes: A Comparison of Methodologies From The Pittsburgh Epidemiology of Diabetes Complications Cohort, Diabetes Research And Clinical Practice, 2011, pp. 280-287.

(56) References Cited

OTHER PUBLICATIONS

Perkins et al., Glycemic Control Is Related To The Morphological Severity Of Diabetic Sensorimotor Polyneuropathy, Diabetes Care, Apr. 2001, pp. 748-752.

Perkins et al., Validation of a Novel Point-of-Care Nerve Conduction Device for the Detection of Diabetic Sensorimotor Polyneuropathy, Diabetes Care, Sep. 2006, pp. 2023-2027.

Perkins et al., Multi-Site Testing With A Point-Of-Care Nerve Conduction Device Can Be Used In An Algorithm To Diagnose Diabetic Sensorimotor Polyneuropathy, Diabetes Care, Mar. 2008, pp. 522-524.

Russell et al., Sural Nerve Myelinated Fiber Density Differences Associated With Meaningful Changes In Clinical And Electrophysiologic Measurement, Journal Of The Neurological Sciences, 1996, pp. 114-117.

Standards Of Medical Care In Diabetes—2006, Diabetes Care, Jan. 2006, pp. S4-S42.

Stetson et al., Effects Of Age, Sex, And Anthropornetric Factors On Nerve Conduction Measures, Muscle & Nerve, Oct. 1992, pp. 1095-1104.

Trojaborg et al., Sural Nerve Conduction Parameters In Normal Subjects Related To Age, Gender, Temperature, And Height: A Reappraisal, Muscle & Nerve, Jun. 1992, pp. 666-671.

Veves et al., The Relationship Between Sural Nerve Morphometric Findings And Measures Of Peripheral Nerve Function In Mild Diabetic Neuropathy, Diabetic Medicine,1991, pp. 917-921.

Vinik et al., Sural Sensory Action Potential Identifies Diabetic Peripheral Neuropathy Responders To Therapy, Muscle & Nerve, Nov. 2005, pp. 619-625.

Vrancken et al., The Realistic Yield Of Lower Leg SNAP Amplitudes And SRAR In The Routine Evaluation Of Chronic Axonal Polyneuropathies, J Neurol, 2008, pp. 1127-1135.

Wald et al., On A Test Whether Two Samples Are From The Same Population, The Annals of Mathematical Statistics, 1940, pp. 147-162.

\* cited by examiner normal operation: no gel-short abnormal operation: with gel-short normal operation: no gel-short abnormal operation: with gel-short

APPARATUS AND METHOD FOR STIMULATOR ON-SKIN SHORT DETECTION

REFERENCE TO PENDING PRIOR PATENT APPLICATIONS

This patent application:

(i) is a continuation-in-part of prior U.S. patent application Ser. No. 13/235,258, now U.S. Pat. No. 9,173,581 filed Sep. 16, 2011 by Bonniejean Boettcher et al. for APPARATUS AND METHOD FOR THE AUTOMATED MEASUREMENT OF SURAL NERVE CONDUCTION VELOCITY AND AMPLITUDE, which in turn claims benefit of:

(a) prior U.S. Provisional Patent Application Ser. No. 61/403,453, filed Sep. 16, 2010 by Shai N. Gozani for NC-STAT® SL;

(b) prior U.S. Provisional Patent Application Ser. No. 61/459,127, filed Dec. 6, 2010 by Shai N. Gozani for NC-STAT® SL;

(c) prior U.S. Provisional Patent Application Ser. No. 61/467,857, filed Mar. 25, 2011 by Shai N. Gozani et al. for NC-STAT® SL;

(d) prior U.S. Provisional Patent Application Ser. No. 61/516,944, filed Apr. 11, 2011 by Bonniejean Boettcher et al. for NC-STAT® SL; and (e) prior U.S. Provisional Patent Application Ser. No. 61/571,203, filed Jun. 22, 2011 by Shai N. Gozani et al. for NC-STAT® DPNCHECK™; and (ii) claims benefit of prior U.S. Provisional Patent Application Ser. No. 61/885,673, filed Oct. 2, 2013 by NeuroMetrix, Inc. and Bonniejean Boettcher et al. for STIMULATOR ON-SKIN SHORT DETECTION.

The seven (7) above-identified patent applications are hereby incorporated herein by reference.

FIELD OF THE INVENTION

This invention relates to apparatus and methods for stimulating living tissue of human subjects, and more particularly to stimulating peripheral nerves in order to determine nerve conduction properties.

BACKGROUND OF THE INVENTION

Diabetes Mellitus ("DM") is a common disease involving ineffective regulation of blood glucose levels. There are over 25 million people in the United States with DM, and recent projections suggest that over 350 million people have the disease worldwide. There are two primary forms of DM. Type I DM generally affects children and young adults and is related to a primary deficiency of the insulin hormone. Type II DM usually affects adults, often over the age of 50, but increasingly in younger adults as well. It is a complex disease that generally starts as a resistance to insulin action that may progress to secondary insulin deficiency. The causes of Type I and Type II DM are not entirely known although genetic, environmental, and lifestyle risk factors have been identified.

Although acutely high or low blood glucose levels are dangerous, the primary sources of DM-associated morbidity and mortality are the long term macrovascular and microvascular complications of the disease. Macrovascular complications refer to cardiovascular events such as myocardial infarction ("heart attack") and stroke. Microvascular complications refer to pathological damage to the nerves, eyes, and kidneys of people with DM.

The most common microvascular complication of DM is neuropathy, or nerve damage. Diabetic neuropathy affects 60% or more of people with DM. Diabetic neuropathy may include damage to the large myelinated nerve fibers, the small myelinated and unmyelinated nerve fibers, and the autonomic nerves. The most common form of diabetic neuropathy is the large fiber form of the disease which is often termed diabetic peripheral neuropathy ("DPN"). DPN leads to pain and disability, and is the primary trigger for foot ulcers which may result in lower extremity amputations.

Because of the severe consequences of DPN, early detection of this complication of DM, and interventions to prevent or slow down progression of the neuropathy, are of paramount importance. Unfortunately, detection of DPN is challenging, particularly at its early stages when it may be most susceptible to intervention. Current methods of detecting and monitoring DPN range from clinical evaluation (including symptoms and signs obtained on simple physical examination) to various tests that include the 5.07/10-g monofilament test (where a column of "fishing line" is pressed into the foot of the patient, with the goal being for the patient to detect the contact before the column of "fishing line" bends), the tuning fork test (where a vibrating tuning fork is placed against the big toe of the patient, with the goal being for the patient to detect the vibration of the tuning fork), and quantitative vibration perception testing (where electronics are used to measure the magnitude of a vibration detectable by the patient). While all of these methods have utility, they are subjective, have inadequate sensitivity or specificity, or both, and have poor reproducibility. The "gold standard" method for evaluation of DPN is a nerve conduction study. In a nerve conduction study, a nerve is electrically stimulated at a first location along the nerve, and then the electrical response of the nerve is detected at a second location along the nerve. Among other things, the rate at which the nerve conducts the signal ("the nerve conduction velocity") and the magnitude of the evoked signal ("the amplitude") are reliable indicators of neuropathy. Unlike the aforementioned techniques, nerve conduction testing is objective, sensitive, specific, and reproducible. As a result, most clinical guidelines suggest confirmation of DPN by nerve conduction testing for a reliable diagnosis.

Despite its technical and clinical attributes, nerve conduction testing is not currently widely used in the detection and monitoring of DPN. The reasons for this include the limited availability, complexity and high cost of the study when performed by specialists, usually a neurologist, using traditional electrodiagnostic equipment. To overcome these obstacles to adoption, a number of devices have been developed to simplify and increase access to nerve conduction studies through automation and other techniques. For example, devices that perform nerve conduction measurements using pre-fabricated, nerve-specific electrode arrays have been developed that largely automate the required technical steps of a nerve conduction study (see, for example, U.S. Pat. No. 5,851,191 issued to Gozani et al. and U.S. Pat. No. 7,917,201 issued to Gozani et al.). Another related solution found in the prior art (see U.S. Pat. No. 5,215,100 issued to Spitz et al.) is an apparatus for the assessment of Carpal Tunnel Syndrome (CTS) in which all the electrodes required to stimulate and record from the nerve are fixed by the device.

These prior art solutions suffer from a number of deficiencies. All devices described in the prior art are either general purpose (i.e., multi-nerve, multi-application) nerve conduction testing devices or they are designed specifically for evaluation of the median nerve for the assessment of CTS. General purpose devices, of necessity, must adapt to the various anatomical and electrophysiological aspects of many different nerves. As a result, only limited customization is possible and the onus remains on the user of the general purpose device to address the sources of variations—such as through the placement of individual electrodes or even pre-configured electrode arrays. As a result, despite simplifying nerve conduction measurements relative to the traditional approaches, the general purpose testing devices still require a fair amount of training in order to properly perform the nerve conduction test procedures. Also, those devices in the prior art specifically designed for the evaluation of the median nerve have little relevance to the requirements of the present invention, which is the assessment of the sural nerve. The primary reason for this is that the anatomy and electrophysiology of the sural nerve (used for the assessment of DPN) is substantially different from that of the median nerve (used for the assessment of CTS). Therefore devices specifically designed for testing of the median nerve cannot be used to test the sural nerve. Another issue with general purpose testing devices is that they require two discrete components—a device with the electronic circuits needed to perform a nerve conduction test, and a nerve-specific electrode array which provides an interface between the unique characteristics of the particular nerve being tested and the common testing device. This two-component requirement limits attempts to reduce test costs, particularly because it restricts the ability to reduce the size of the electrode array, which is a primary cost driver in nerve conduction testing.

More recently, a fully-integrated, hand-held sural nerve conduction testing device has been developed to overcome some of the deficiencies of prior art testing devices (i.e., see, for example, the aforementioned U.S. patent application Ser. No. 13/235,258). The fully-integrated, hand-held sural nerve conduction testing device disclosed in U.S. patent application Ser. No. 13/235,258 is designed and optimized for testing of the sural nerve. As a result, the nerve conduction test procedure has been substantially simplified and automated to the point where the procedure can be taught to someone in 30-60 minutes, after which the trained person should be able to obtain accurate sural nerve conduction results. Further, due to its focused application on the sural nerve, the nerve conduction test procedure has been automated to the point where the test duration is typically only 15-30 seconds in length. Another benefit of the focused application on the sural nerve is that the costs of both the hardware and disposable components have been substantially reduced relative to a general purpose nerve conduction testing device.

One potential deficiency of the sural nerve conduction testing device disclosed in U.S. patent application Ser. No. 13/235,258 is that stimulator probes on the skin can be shorted or shunted during nerve conduction testing when gel on the skin creates an alternative conductive path between the two probes. A short condition refers to an alternative path carrying all of the simulation current. A shunt condition refers to an alternative path carrying a portion of the stimulation current. For example, shorting or shunting between the anode and the cathode stimulator probes of the device can be caused by an inexperienced user applying excessive amounts of conductive gels on the testing area when preparing for the sural nerve conduction test. When gel short or shunting occurs, the alternative conductive path may cause insufficient nerve stimulation and/or inaccurate nerve conduction parameters being reported due to falsely-low recorded nerve response.

SUMMARY OF THE INVENTION

The present invention overcomes the problem of reporting potentially inaccurate nerve conduction parameters by detecting a stimulator probe short or shunt condition during nerve conduction study testing.

Detection of a short or shunt condition between two stimulator probes is accomplished by monitoring the following conditions:

(1) the magnitude of the stimulus artifact waveform; and (2) the voltage difference between the anode probe and the cathode probe of the stimulator.

More particularly, when the magnitude of the stimulus artifact waveform is below a first threshold and the voltage difference between the anode probe and the cathode probe of the stimulator is below a second threshold, the nerve conduction test is flagged, the device displays a message to the tester and no nerve conduction study parameters are provided to the tester, in order to prevent reporting inaccurate nerve conduction parameters derived from nerve responses recorded after inadequate nerve stimulation due to a short or shunt condition between the stimulator probes.

In one preferred form of the invention, there is provided a device for measuring sural nerve conduction velocity and amplitude, the device comprising:

a housing;

stimulation means mounted to the housing for electrically stimulating a human sural nerve;

a biosensor releasably mounted to the housing, the biosensor comprising a plurality of electrodes for detecting a sural nerve response evoked by the stimulation means;

acquisition means mounted to the housing and electrically connected to the biosensor for electrically acquiring the sural nerve response detected by the biosensor;

detection means mounted to the housing and electrically connected to the stimulation means and the acquisition means for detecting shorting or shunt of the stimulation current on the surface of the skin;

processing means mounted to the housing and electrically connected to the acquisition means for digitizing, processing and storing the acquired sural nerve response;

calculation means mounted to the housing and electrically connected to the processing means for calculating the conduction velocity and amplitude of the processed sural nerve response; and display means mounted to the housing for displaying the sural nerve conduction velocity and amplitude;

wherein the stimulation means and the biosensor are designed to be placed on a patient's anatomy, in the vicinity of a sural nerve, by manipulating the housing.

In another preferred form of the invention, there is provided a method for measuring nerve conduction attributes, the method comprising:

positioning a nerve conduction testing device on the surface of the skin of a patient so that the nerve conduction testing device is positioned to electrically stimulate a nerve and a biosensor is positioned to detect a nerve response evoked by the nerve conduction testing device;

detecting the likelihood of shorting or shunting of the stimulation current on the surface of the skin;

using the nerve conduction testing device to electrically stimulate a nerve and to acquire the nerve response detected by the biosensor; and processing the acquired nerve response to determine the conduction attributes of the processed nerve response.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Device Description

Figure 1:
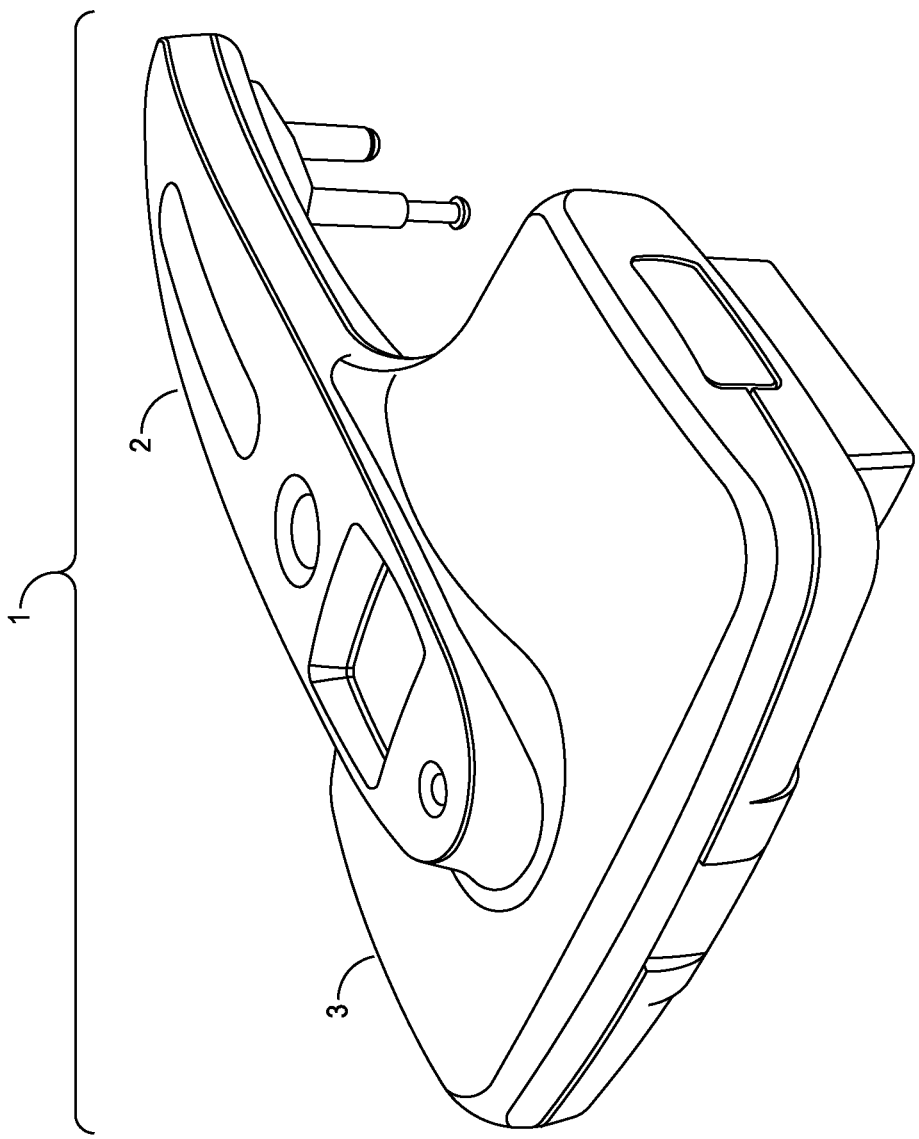
FIG. 1 is a schematic view of a novel, fully-integrated, hand-held sural nerve conduction testing device formed in accordance with the present invention.

The present invention is a fully-integrated, hand-held sural nerve conduction testing device. The device is designed exclusively for non-invasive nerve conduction measurements of the human sural nerve in the region of the lower calf and ankle. The sural nerve is an almost-entirely sensory nerve formed from the merger of the medial and lateral sural cutaneous nerves which are branches of the tibial and common fibular nerves (which are themselves branches of the sciatic nerve). After forming at the distal third of the gastroc muscle, the sural nerve runs down the leg on the posterior-lateral side, then posterior to the lateral malleolus where it runs deep to the fibularis tendon sheath and reaches the lateral tuberosity of the fifth toe, where it ramifies. The sural nerve transmits sensory signals from the posterior lateral corner of the leg, the lateral foot and the 5th toe.

Sural nerve conduction is a standard and quantitative biomarker of DPN. Sural nerve conduction testing detects DPN with high diagnostic sensitivity and reveals abnormalities before there is clinical evidence of neuropathy. Sural nerve conduction is correlated to the morphological severity of myelinated fiber loss and is therefore predictive of foot ulcer risk.

There are a variety of nerve conduction methodologies by which the sural nerve can be evaluated. For example, the nerve can be tested orthodromically by stimulating the nerve at the ankle and then measuring the nerve response after it has conducted a known distance up the calf, or the nerve can be tested antidromically by stimulating the nerve in the calf and then measuring the nerve response after it has conducted a known distance to the ankle. Another methodological factor in nerve conduction testing for the sural nerve includes the distance between the points of stimulation and recording, which generally varies from about 8 cm to 16 cm. Another methodological factor associated with nerve conduction testing of the sural nerve is the configuration of the recording electrodes, including their shape, size, and the distance between them. In the preferred embodiment of the present invention, the sural nerve is tested orthodromically with a stimulation-to-recording distance of 9.22 cm. The preferred recording electrode configuration is provided below in the description of the biosensor.

The purpose of the present invention is to easily, rapidly, accurately, and reliably measure and report two common sural nerve conduction parameters: the onset conduction velocity (hereafter abbreviated as "CV") and the sensory response amplitude (hereafter described as "amplitude"). The term "fully-integrated" indicates that all of the components needed for performing a nerve conduction test of the sural nerve are incorporated into a single physical unit, as opposed two or more distinct components (for example, an electrode array and a testing instrument connected by a cable). The term "hand-held" indicates that the device is applied to the patient by a qualified user in order to test the nerve, rather than being a fixed apparatus into which the patient places their limb. The "fully-integrated" and "hand-held" characteristics require technological advances that are both novel and non-obvious. To improve the reliability of the acquired nerve conduction parameters, the present invention incorporates a method to detect shorting and shunting between stimulator probes that might compromising the accuracy of the nerve conduction parameters. Stimulator probe shorting and shunting is primarily caused by user error with excessive conductive gel being used in the skin area where the stimulator probes are placed.

An overall view of the present invention is provided in FIG. 1. As shown, the invention comprises a single fully-integrated, hand-held device 1 with a narrow handle 2 and a head 3. In the preferred embodiment, device 1 is 19.0 cm in length and 11.5 cm in width at its widest point on head 3. The most critical dimension is the distance between cathode 10 (FIG. 3) of device 1 (which is the point of nerve stimulation) and the center of the electrodes 41, 43 on the biosensor 30. When biosensor 30 is seated in the biosensor port 16 (FIG. 3), electrodes 41, 43 are closest to cathode 10. That distance (i.e., the distance between cathode 10 and electrodes 41, 43) represents the conduction distance between the point of nerve stimulation via cathode 10 and arrival of the evoked nerve impulse at electrodes 41, 43. This distance is 9.22 cm in the preferred construction and is used to calculate the CV as will be described below.

Figure 2:
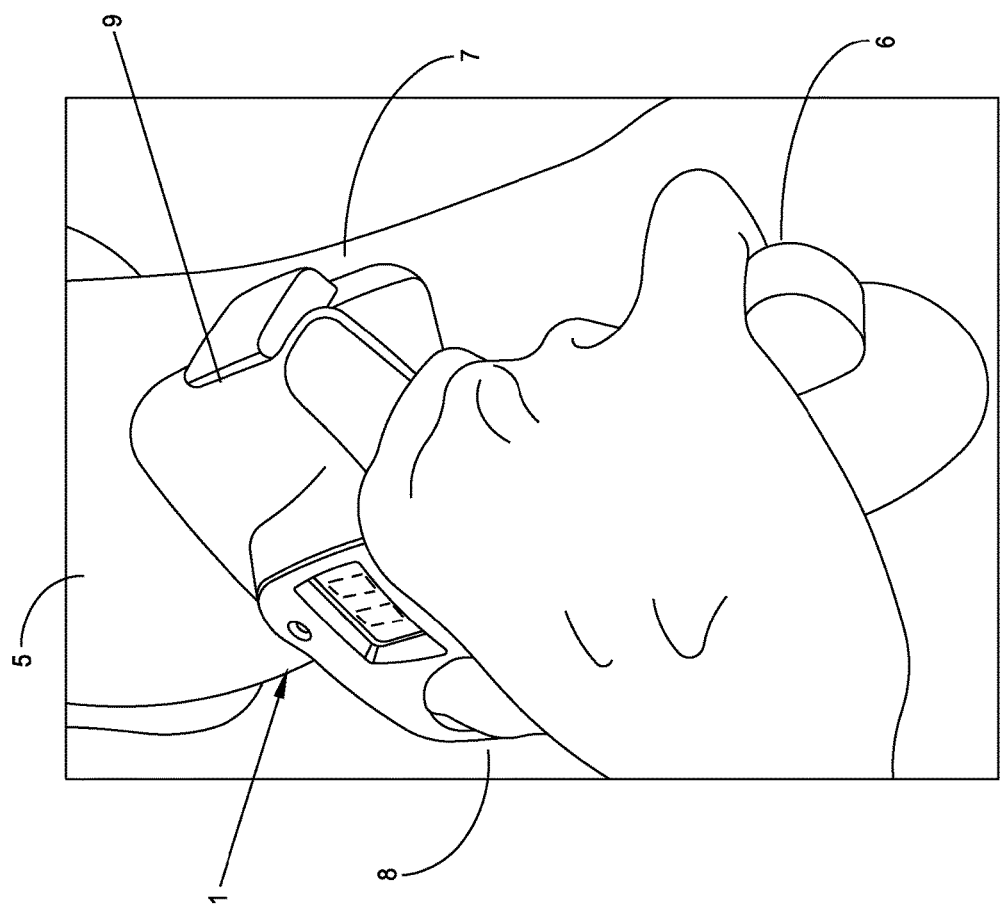
FIG. 2 is a schematic view showing the testing device of FIG. 1 being placed on a patient's limb.

A preferred use of the invention is shown in FIG. 2. As shown, device 1 is placed against the lateral aspect of the patient's lower leg 5 such that (i) the stimulation probes 10, 11 (FIG. 3) mechanically contact the leg immediately behind the outside ankle bone ("lateral malleoulus") 6, and (ii) biosensor 30 contacts the patient's lower calf 7, with the inner edge (one of the two sides 8 or 9, depending on the limb) of device 1 being approximately aligned with the Achilles tendon. In order to reliably measure nerve conduction of the sural nerve, device 1 must have enough degrees of freedom in order to conform to the patient's lower leg anatomy and thereby allow for robust and stable contact of certain device components (i.e., the stimulating electrodes and the detecting electrodes) with the patient. The means to accomplish this robust electrical contact are described in detail below.

Figure 3:
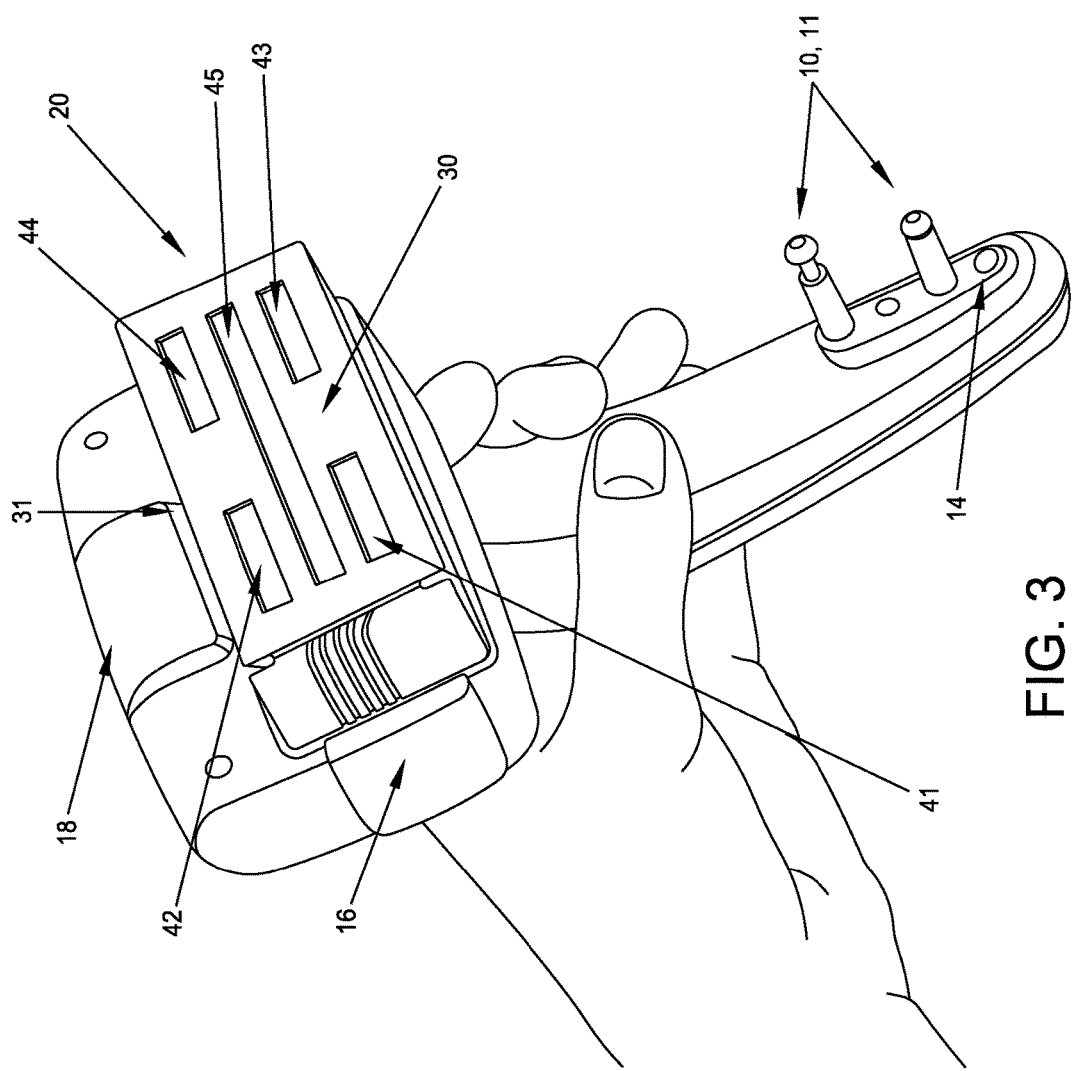
FIG. 3 is a schematic view of the bottom of the testing device shown in FIG. 1.

FIG. 3 is a bottom view of the preferred embodiment of device 1. This view shows the surfaces that contact the patient. There are two stainless steel probes 10, 11 for electrically stimulating the sural nerve when device 1 is placed against the patient in the manner shown in FIG. 2. The cathode 10 has a variable height relative to handle 2 due to its spring-loaded construction. In the preferred embodiment this variable height ranges from 2.5 cm (compressed condition) to 3.3 cm (uncompressed condition) from handle 2. The anode 11 preferably has a fixed height relative to handle 2, which in the preferred embodiment is fixed at 2.3 cm from the handle. The variable length cathode 10 is novel inasmuch as it provides a degree of freedom to enable robust contact of both stimulating probes 10, 11 with the patient anatomy in the vicinity of the ankle, which is non-planar and has a topology which varies from patient to patient. Although it is possible to electrically stimulate the sural nerve through the stimulating probes 10, 11 by direct contact with the patient's skin, it is preferable to use a small amount of conductive hydrogel on the outer tip of each probe so as to reduce the impedance of the probe-skin interface.

Device 1 includes an infra-red thermometer 14 (FIG. 3) for non-contact measurement of the patient's skin surface temperature in the vicinity of the ankle bone. As will be discussed below, this temperature measurement is used to compensate for the effects of temperature on nerve conduction results. The use of a non-contact temperature measuring device is an important aspect of the present invention, since it permits reliable temperature measurements to be made in the irregular skin surface topology associated with the sural nerve.

Figure 4:
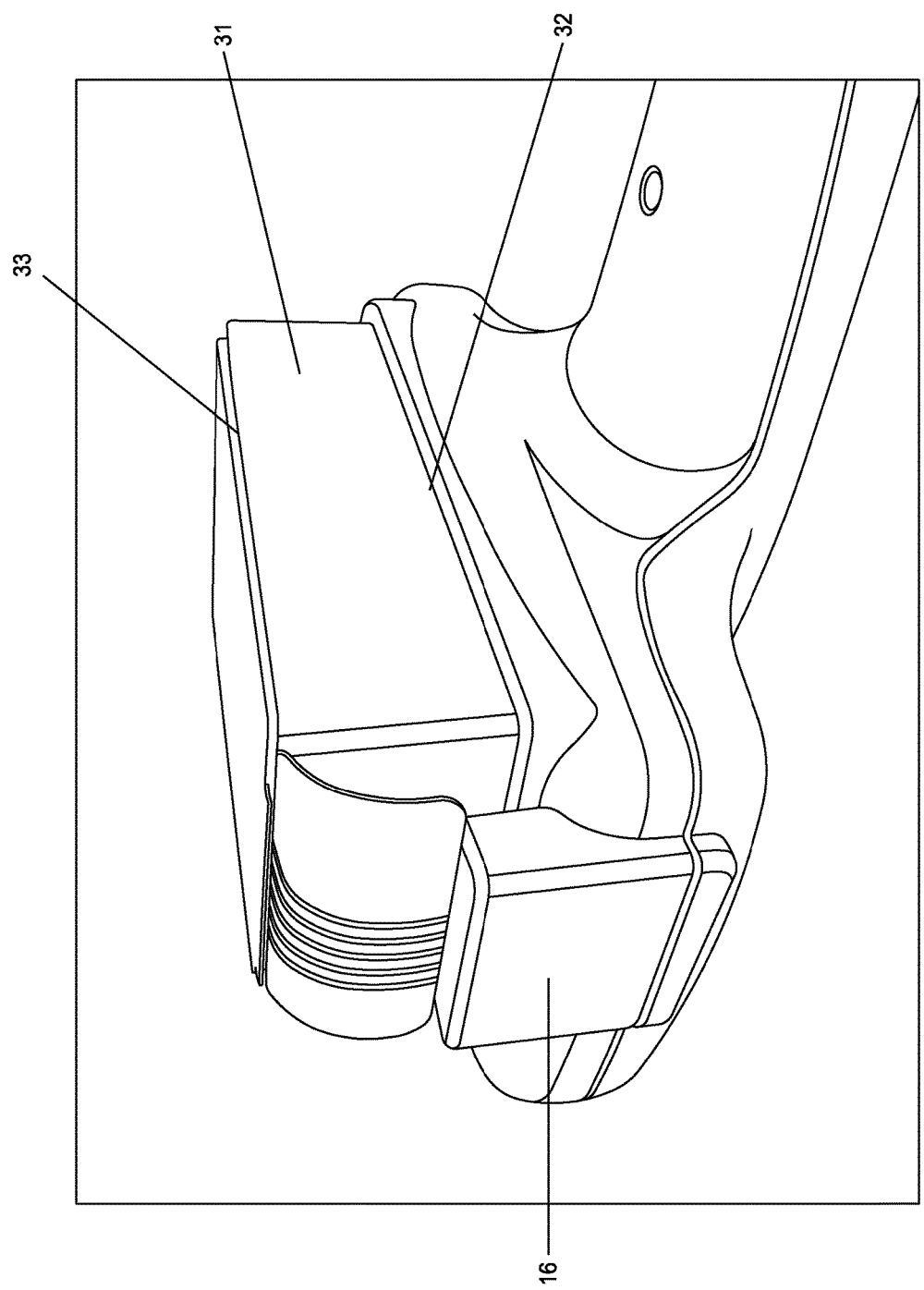
FIG. 4 is a schematic view showing selected portions of the testing device of FIG. 1, including the biosensor, foam pad, and device head.

Head 3 of device 1 supports biosensor 30, which provides a bioelectrical interface to the patient. Biosensor 30, which is described in detail below, is disposable and should be replaced between patients. Biosensor 30 is secured to device 1 by a foam pad 31 (FIGS. 3 and 4) which is provided with non-permanent adhesive on both sides of the foam pad—the adhesive on the inner surface of foam pad 31 releasably secures the foam pad to head 3 of device 1, and the adhesive on the outer surface of foam pad 31 releasably secures biosensor 30 to the foam pad. Foam pad 31 is disposable but may be used for multiple patients as it does not come in direct contact with the patient. Foam pad 31 is shown in greater detail in FIG. 4. One side 32 of the foam pad attaches to the bottom surface of head 3 of device 1, and the other side 33 attaches to the non-patient contact side of biosensor 30. In the preferred embodiment, foam pad 31 is 2.2 cm thick. Although various types of foam may be used, in the preferred embodiment, polyurethane foam is used. When device 1 is pressed against the patient's leg as shown in FIG. 2, the foam pad provides multiple degrees of freedom by which biosensor 30 may conform to the patient's anatomy so as to establish complete contact with the patient's skin. A uniform and complete contact between electrodes 41, 42, 43, 44 and 45 (FIG. 3) and patient skin makes it possible to acquire high quality nerve conduction signals over a wide variety of patient anatomy. The use of foam pad 31 in achieving a uniform and complete contact of electrodes and patient skin is novel and non-obvious. Biosensor 30 is connected to the internal electronics of device 1 via biosensor port 16.

Thus it will be seen that device 1 includes (i) novel means for ensuring reliable electrical contact between the stimulating electrodes and the skin of the patient (i.e., the spring-loaded cathode 10 and the fixed-position anode 11), and (ii) novel means for ensuring reliable electrical contact between the detecting electrodes and the skin of the patient (i.e., the use of foam pad 31 to support biosensor 30).

Head 3 of device 1 includes a battery compartment 18 (FIG. 3) with a removable door for replacement of the battery 109 (FIG. 8), which in the preferred embodiment is a widely available 3V Lithium Ion battery (CR123A). A mini USB port 20 (FIG. 3) allows for device 1 to communicate with external devices (such as a PC) using the standard USB protocol.

Figure 5:
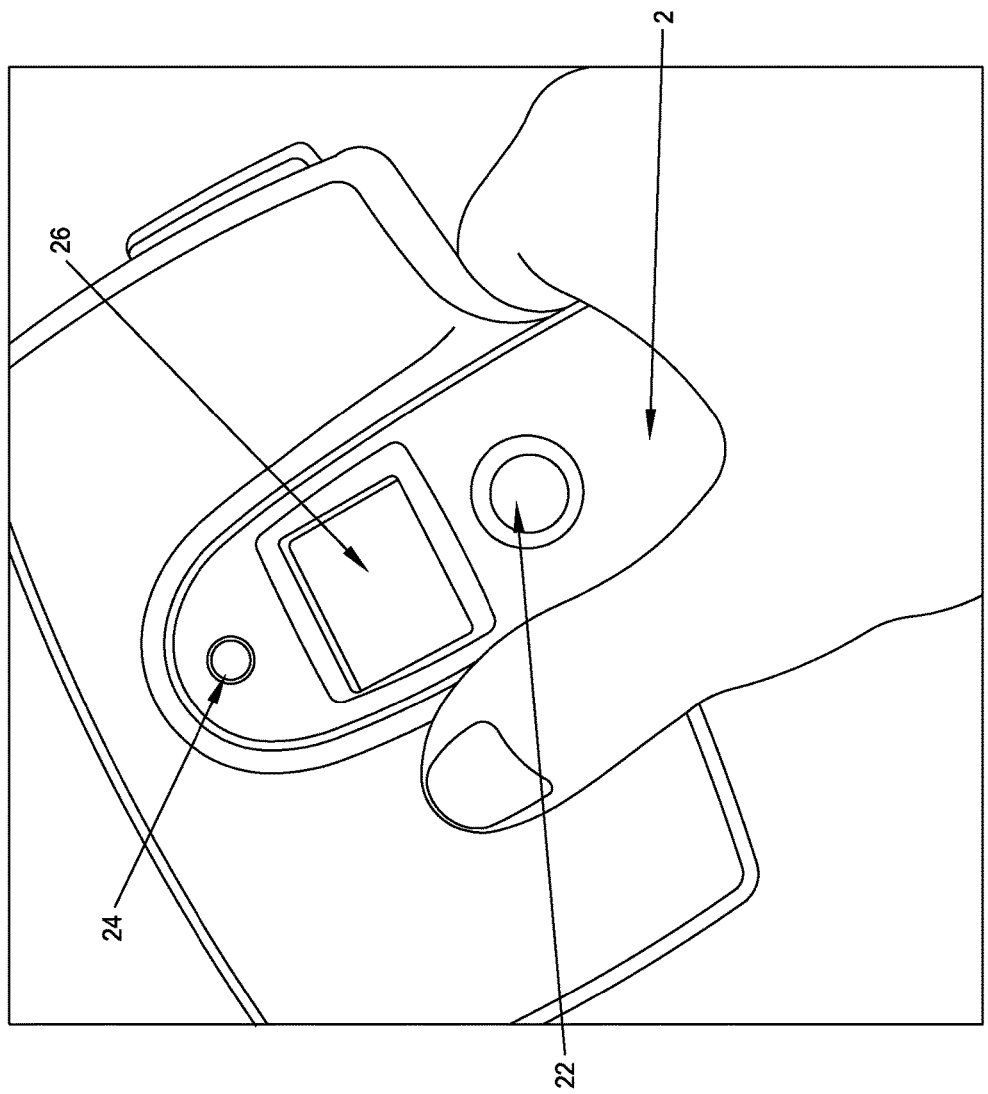
FIG. 5 is a schematic view of the top of the testing device shown in FIG. 1.

FIG. 5 shows the top of device 1, which provides the user interface. In the preferred embodiment, the user interface consists of one push-button switch 22, an LED 24, and an LCD 26. Push-button switch 22 turns on device 1 if the device is powered off. If device 1 is powered on, then switch 22 initiates a nerve conduction test. LED 24 has three colors (green, amber, and red) and is used to indicate device status, which may include green to represent "ready to test," amber to indicate "battery low," and red to indicate "error—cannot perform test." In the preferred embodiment, LCD 26 is a two 7-segment display with additional dot indicators. LCD 26 displays the results of the sural nerve conduction test or an error status to the user as shown at 180 in FIG. 12. A successful test is accompanied by a toggling display on the LCD of (i) the numerical values of the CV, and (ii) the amplitude of the nerve response (or an amplitude of 0, without a CV, to indicate that sural nerve conduction is not detectable). An unsuccessful test is accompanied by an error status message 180 (see FIG. 12) on LCD 26 which indicates the probable cause for the failure. In the preferred embodiment, the error status messages include "Sn" for an error related to the biosensor, "Er" for an error related to excessive muscle interference, "Pr" for an error related to stimulating probes, and "° C." for an error related to patient skin surface temperature.

Hardware Description

Figure 8:
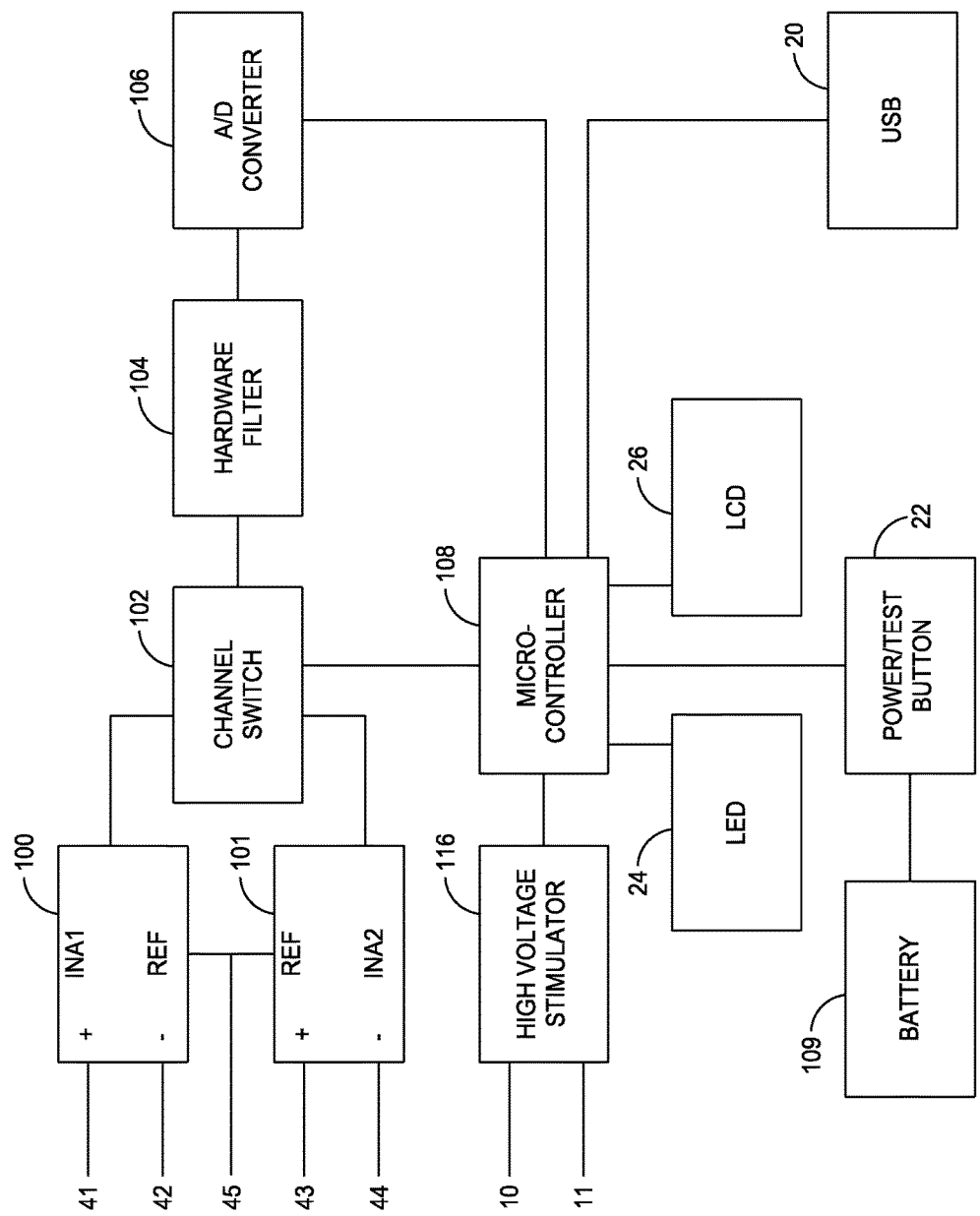
FIG. 8 is a high level hardware schematic of the testing device shown in FIG. 1.

FIG. 8 is a block diagram of a preferred embodiment of the internal electronics (hardware) of device 1. The hardware consists of two instrumentation amplifiers (INA) 100, 101 with differential inputs coming from the two pairs of active electrodes 41, 42 and 43, 44. In the preferred embodiment, these INAs have a typical input impedance$\geq 10^{10}$ (10 to the $10^{th}$ power) Ohms and a common mode rejection ratio$\geq 90$ dB. The INAs 100, 101 share a common reference input coming from reference electrode 45. The outputs of INAs 100, 101 are fed into a 2×1 switch 102 that determines which of the two channels will be acquired and processed. Switch 102 is controlled by the microcontroller 108, with the channel selection determined by the test control software (see below). The channel selection may be different at different stages of the testing. The output of switch 102 is input into a band-pass filter 104. In the preferred embodiment, band-pass filter 104 has a low frequency cutoff of 2 Hz and a high frequency cutoff of 4900 Hz. The output of band-pass filter 104 is then digitized by the A/D converter 106, with the digital output going into the microcontroller 108 for storage and processing.

Microcontroller 108 triggers the high voltage stimulator 116 to deliver nerve stimulation to the patient via cathode 10 and anode 11. In a preferred embodiment, the high voltage stimulator 116 is a constant current stimulator that generates a monophasic square DC pulse with a duration of 50 to 100 μsecs. The output voltage of the high voltage stimulator is 400-440 V, with a typical value of 420 V. The high voltage stimulator is capable of delivering up to 100 mA into a 3.3 kOhm load.

Microcontroller 108 controls the user interface components including LED 24, LCD 26, and power/test button 22. Microcontroller 108 also communicates with an isolated USB port 20 (FIG. 3) for external communication (such as with a PC). The internal electronics of device 1 are powered from a single battery 109. In the preferred embodiment, this is the commonly-available 3V Lithium battery CR123A.

Principles Of Operation

A nerve conduction test is performed on the patient by placing device 1 against the patient in the manner shown in FIG. 2 and described above. When in this disposition, cathode 10 is located over the sural nerve as the sural nerve passes behind the lateral malleoulus 6 (FIG. 2), and biosensor 30 is located over (or in a worst case, adjacent to) the sural nerve as the sural nerve approaches the Achilles tendon, about 9 cm from cathode 10. The distance from stimulating cathode 10 to the electrode is 9.22 cm, and this is the distance used to determine the conduction velocity.

Software

Figure 12:
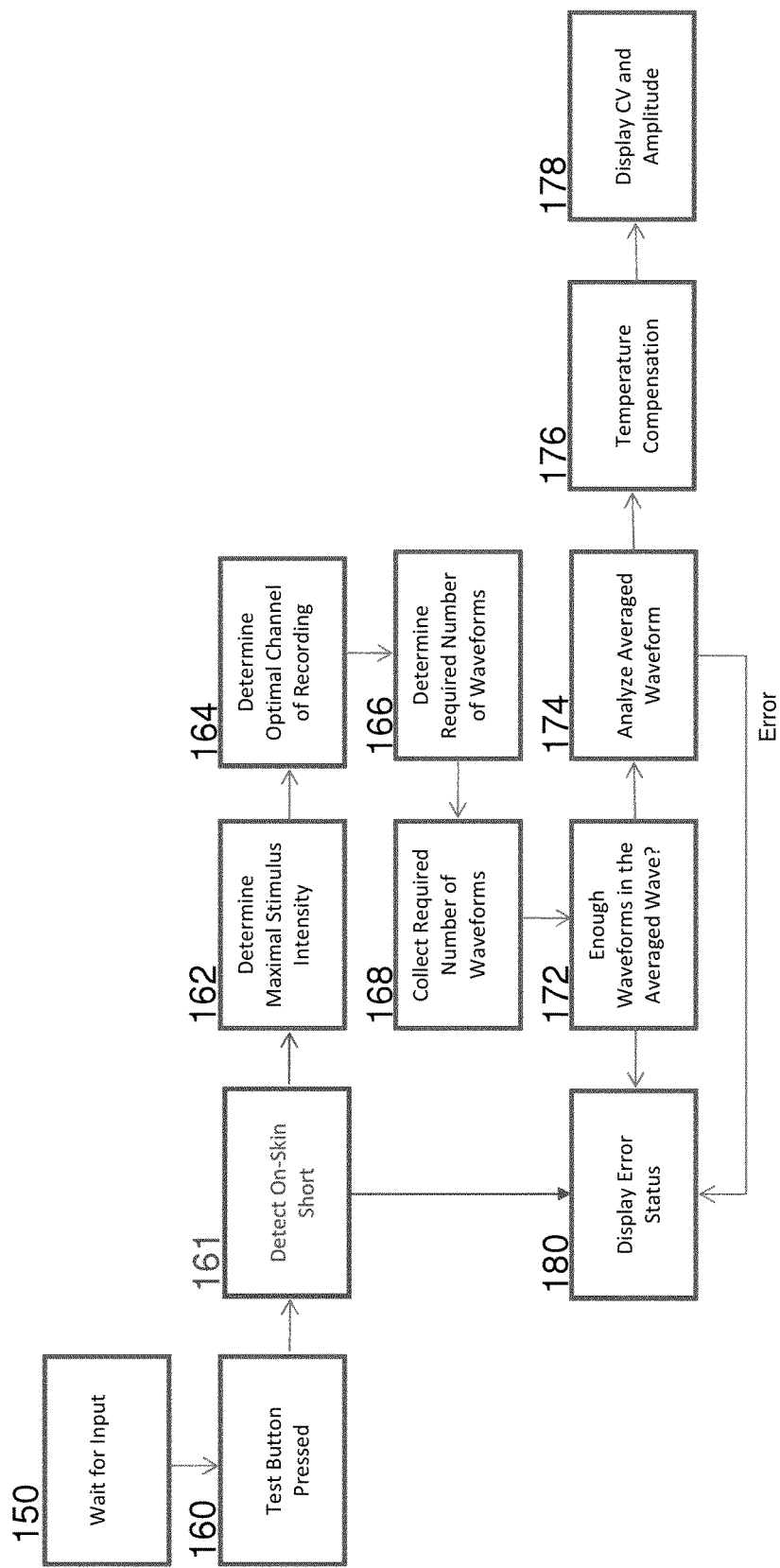
FIG. 12 is a high level functional schematic of the preferred control algorithm for the testing device of FIG. 1.

Device 1 is controlled by a software-based control algorithm which resides on microcontroller 108 (or, alternatively, on an associated storage unit). FIG. 12 provides an overview of various functional blocks of the control algorithm. Upon power up, the control algorithm is in state 150 and waits for an external event, which in the preferred embodiment is test button pressed.

Test Button Pressed

This part of the control algorithm is executed when test button 22 (FIG. 5) is pressed. Upon detection of this event (function block 160), the control algorithm goes into the test control module which implements a sural nerve conduction test. A sural nerve conduction test is comprised of several sequential steps as described below.

STEP 1. Adequate nerve stimulation is critical to the accurate assessment of the nerve conduction properties of the sural nerve. The device 1 is capable of delivering up to 100 mA of constant current through its stimulator probes. However, if a superficial alternative current path exists in addition to the expected current path passing through the sural nerve, one can no longer be certain of the actual current flowing through the tissue surrounding the sural nerve. It is therefore important to verify that no such alternative current path exists during a nerve conduction test.

As a part of the nerve conduction testing, the tester may elect to apply a small amount of conductive gel on the tip of the stimulator probes to facilitate stimulation of the sural nerve. The preferred embodiment of the high voltage stimulator is capable of delivering up to 100 mA into a 3.3 kOhm load. Depending upon the skin condition of the patient, the stimulator probe-skin interface 210 may have very high impedance (FIG. 9A). If the impedance of the stimulator probe-skin interface 210 is too large, the magnitude of the stimulation current may not reach 100 mA. Conductive gel 220 reduces the impedance of the stimulator probe-skin interface 210 to ensure adequate delivery of the stimulation current for testing patients with a variety of skin conditions.

If the amount of conductive gel applied to the stimulator probes is excessive, the conductive gel may form an alternative conductive path 225 (FIG. 9B) between the stimulator probes in addition to the desired current pathway 230 for nerve stimulation.

Figure 9C:
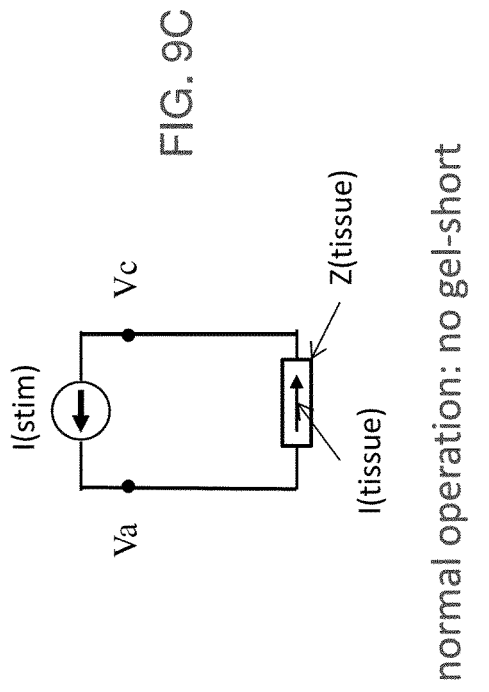
FIGS. 9A-9D are schematic views showing normal operation with no gel-short (FIG. 9A) and abnormal operation with gel-short (FIG. 9B) on the skin, and corresponding circuit models of normal operation with no gel-short (FIG. 9C) and abnormal operation with gel-short (FIG. 9D)
Figure 9D:
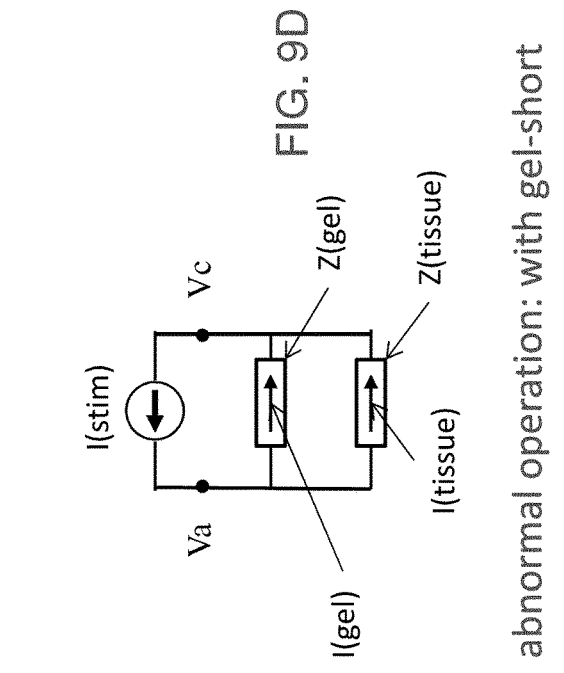
Figure 9A:
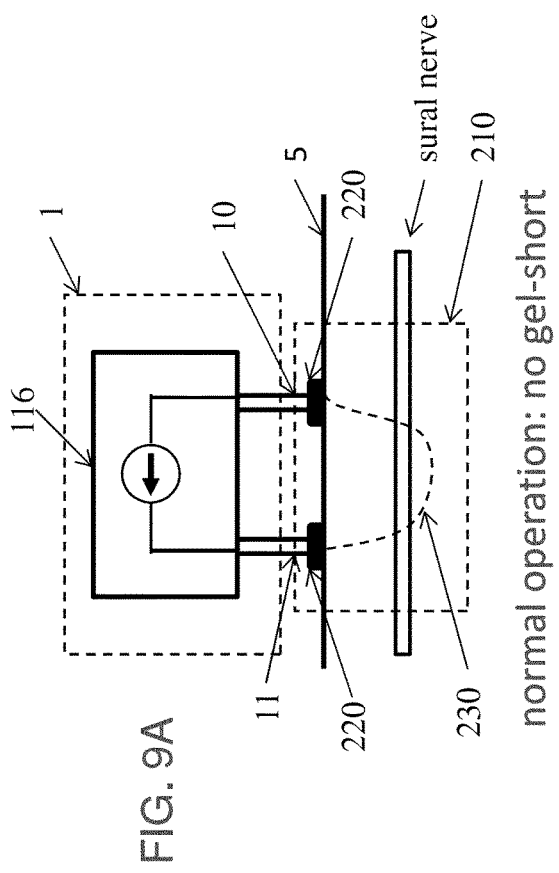
Figure 9B:
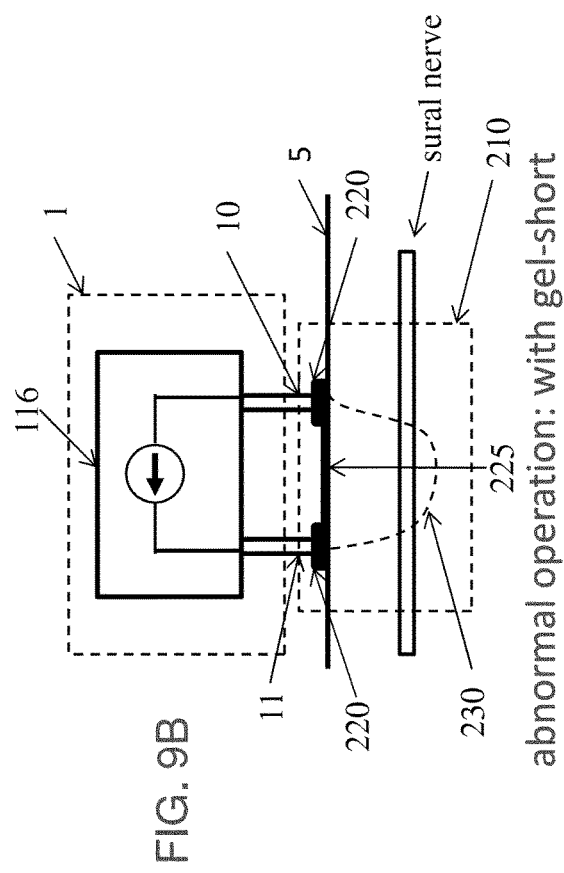

To illustrate this problem more precisely, a simplified equivalent circuit model for a normal nerve stimulation and gel-shorted nerve stimulation are shown in FIGS. 9C and 9D, respectively. Under the normal nerve stimulation condition (FIGS. 9A and 9C), stimulation current flowing through the region of tissues surrounding the sural nerve, I(tissue), is the same as the stimulator current I(stim). Therefore, the nerve conduction device has a complete control over the adequacy of the nerve stimulation current. When a gel-short condition is created (FIGS. 9B and 9D), the I(stim) is divided into two paths signified by their respective impedance: Z(gel) and Z(tissue). Often the impedance Z(gel) is much smaller than the impedance of Z(tissue), causing a large portion of the I(stim) to flow through Z(gel) as I(gel). The current I(gel) will have no effect on nerve stimulation. The current I(tissue)=I(stim)−I(gel) is the amount of current that flows through Z(tissue) which is relevant to nerve stimulation.

By examining only the current from the stimulator, one cannot determine whether an alternative conductive path is created, since the stimulator only "sees" the total current I(stim) flowing out of or into the two stimulator probes. The present invention discloses a method to detect the presence of an alternative conductive path based on the voltage difference between the anode and cathode stimulator probes and the characteristics of the waveform acquired from the recording electrodes.

Figure 6:
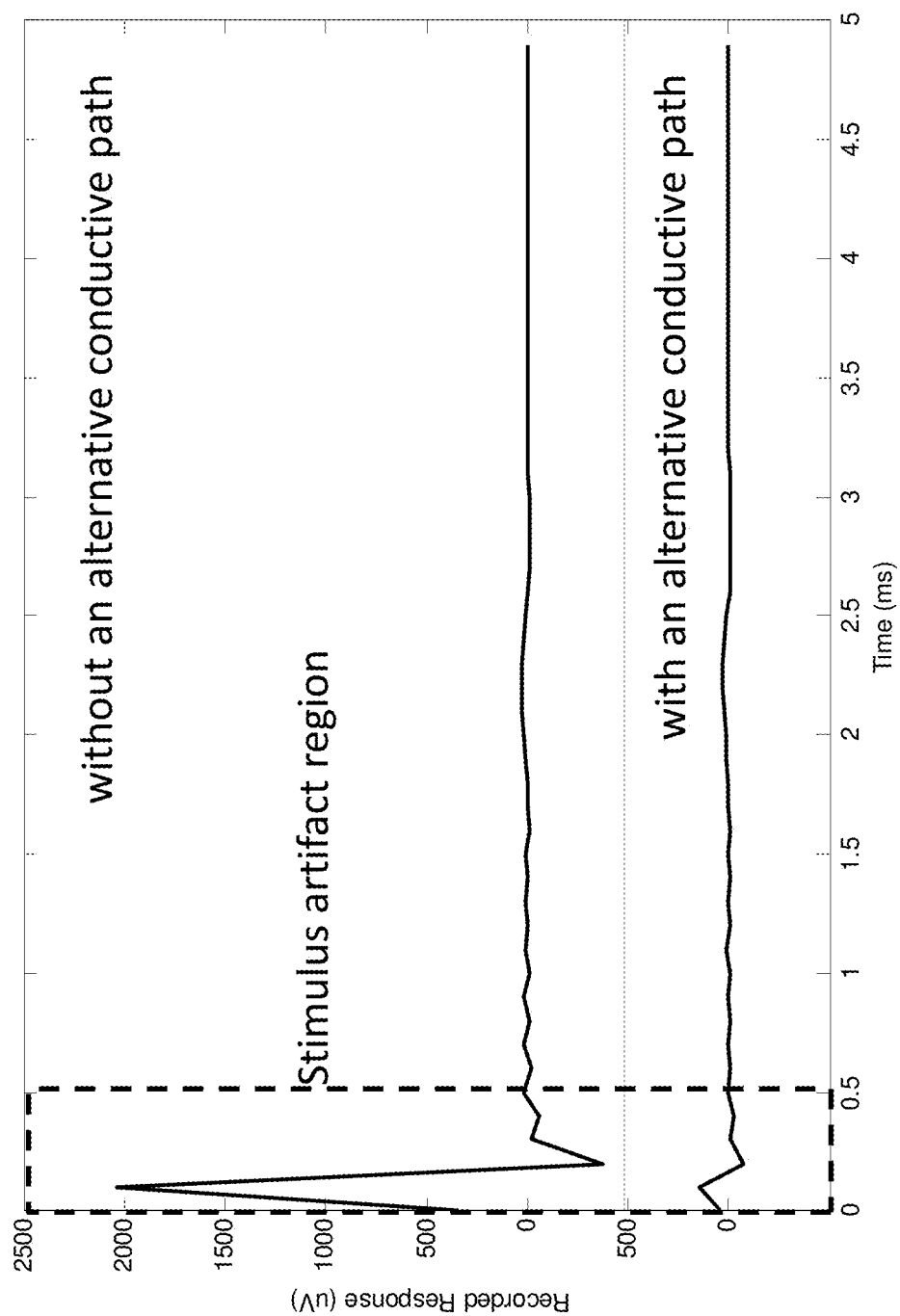
FIG. 6 is an example of stimulus artifacts recorded with data acquisition means with and without an alternative conductive path on the skin surface.

In a preferred embodiment, a stimulation current I(stim) of 20 mA is used to detect the presence of an alternative conductive path caused by excessive conductive gel or other conductive materials on the surface of the skin. In the preferred embodiment, the anode voltage Va is held constant at 400 volts. To create a larger voltage difference between the two stimulator probes (anode and cathode), the cathode probe voltage Vc is reduced via microcontroller 108 (FIG. 8). When an alternative path Z(gel) is present, the total impedance seen by the stimulator is smaller than the case when Z(gel) is absent. According to electronic circuit theory, Vc=Va−I(stim)*[Z(gel)//Z(tissue)](symbol "//" indicates parallel relationship between two impedance components) will be much higher than Vc=Va−I(stim)*[Z(tissue)]. To add specificity to the above detector, the stimulus artifact portion of the data recorded from the detection electrodes is also examined. When there is no alternative conductive path (i.e., Z(gel)=infinite), the stimulus artifact size is on the order of several thousand microvolts. When an alternative conductive path exists due to excessive conductive gel on the skin forming the alternative conductive path, the stimulus artifact size is much smaller (e.g., on the order a few hundred microvolts). In the preferred embodiment, stimulus artifact size is the largest absolute value of the recorded signal in the stimulus artifact region and the region is defined as the first 0.5 milliseconds following the onset of the stimulation pulse (see FIG. 6).

Figure 7:
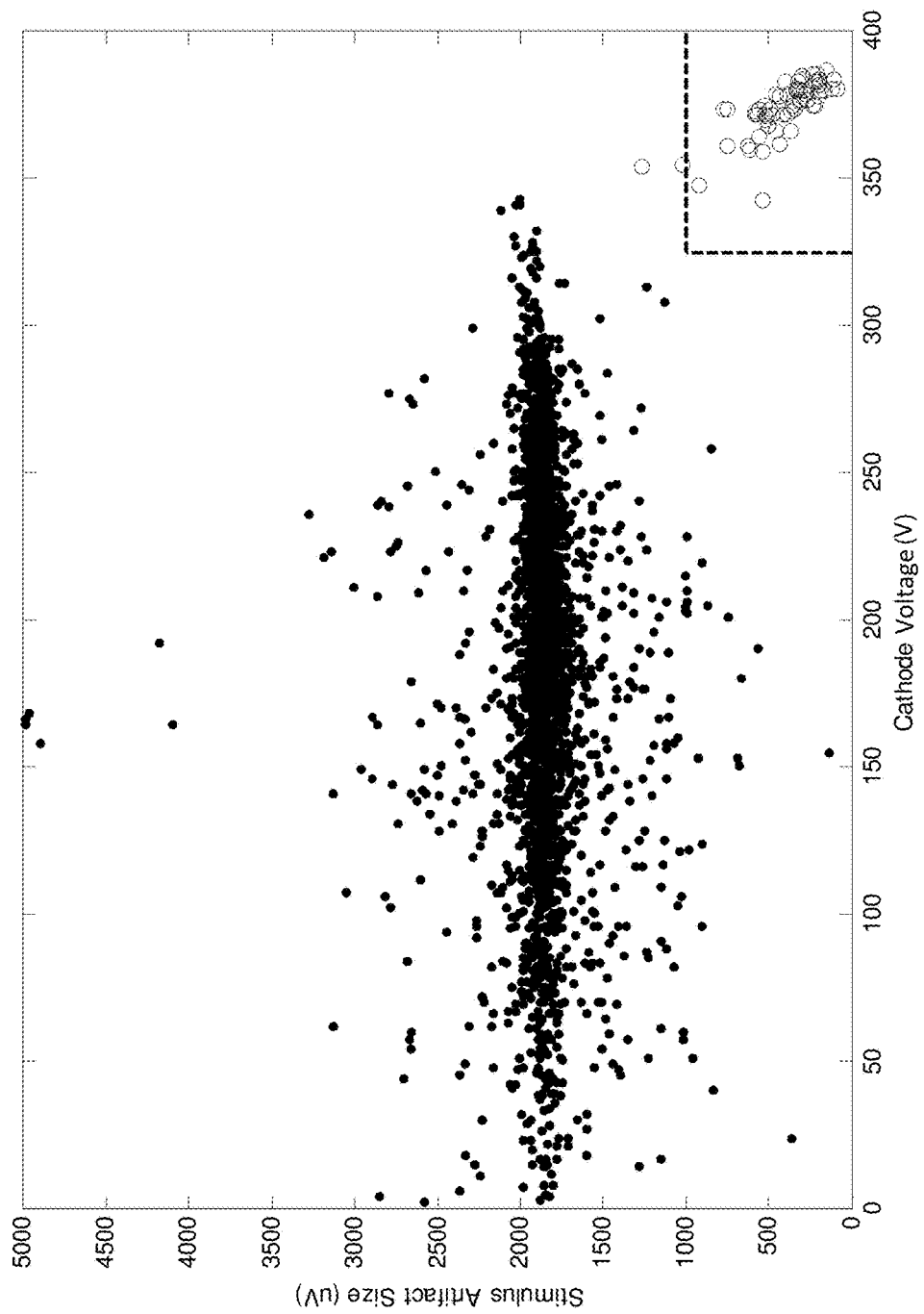
FIG. 7 is an example of how to determine whether an alternative conductive path on the skin exists.

Experiments were conducted to validate the foregoing construction. A total of 2,933 tests without gel short and 63 tests with gel shorts were conducted on more than 700 subjects with a wide range of skin conditions. The scatter plot in FIG. 7 clearly illustrates the effectiveness of the preferred embodiment where the threshold for stimulus artifact size is set at 1000 microvolt and the cathode voltage is set at 325 volts (while the anode voltage is held at 400 volts). It has a detection accuracy of 99.93%. Only two cases of gel shorts were missed.

It is noted that Z(gel) and Z(tissue) have distinct characteristics in terms of relative strength of capacitive and resistive components, in addition to the difference in absolute values of the impedance. Consequently, the decaying rates of the stimulus artifact are different depending upon whether the alternative conductive path Z(gel) exists or not. One can utilize differences in decaying rates to detect the existence of an alternative conductive path (i.e., shorting or shunting on the skin due to excessive conductive gel).

When shorting or shunting on the skin is detected (function block 161 in FIG. 12), the device will stop the nerve conduction testing and provide the user with a message for checking potential source of shorting of stimulator probes.

STEP 2. Proper measurement of nerve conduction requires that the nerve is stimulated at the "maximal" level. This "maximal" level is defined as the stimulus intensity such that further increasing of the intensity of the stimulus does not increase the nerve response. In the preferred embodiment (function block 162), this is accomplished by sequentially increasing the stimulus intensity from 20 mA to 60 mA in 10 mA steps. Starting with 30 mA and with each succeeding stimulus intensity, the last two nerve responses are compared with one another. If they are similar in amplitude and shape, as determined by their correlation to one another and to a generic sural nerve response template, then the stimulus intensity is considered to be maximal. In the preferred embodiment, the correlation is implemented as a sum of the products of the two response waveforms (or a response waveform and a generic template), normalized by the square root of the product of the energy in each response waveform (or a response waveform and a generic template). However, if desired, similarity measures different from the correlation technique mentioned above may also be used. If a maximal stimulus intensity is not found, then subsequent data collection is performed at 60 mA.

STEP 3. If desired, the two electrode pairs 41, 42 and 43, 44 may be compared during STEP 2 to determine which of the two electrode pairs overlies the sural nerve and therefore constitutes the optimal recording channel. Details of how to determine the optimal recording channel (function block 164 in FIG. 12) are set forth in further detail in the aforementioned U.S. patent application Ser. No. 13/235,258, which patent application is hereby incorporated herein by reference.

STEP 4. Upon determination of the maximal stimulus intensity level, device 1 will repeatedly stimulate the sural nerve at the maximal stimulus intensity level and average the nerve responses into a mean nerve response. In the preferred embodiment (function blocks 166, 168 and 172 in FIG. 12), the number of waveforms averaged is either 4 or 8 depending on the estimated signal-to-noise ratio of the first nerve response obtained at the maximal stimulus intensity level. If the signal-to-noise ratio is low, then 8 responses are averaged, and if the signal-to-noise ratio is high, then 4 responses are averaged. During waveform averaging, device 1 will exclude responses that are "outliers". In the preferred embodiment of the present invention, outliers are determined by comparing a given response to the running average of prior responses.

Figure 10:
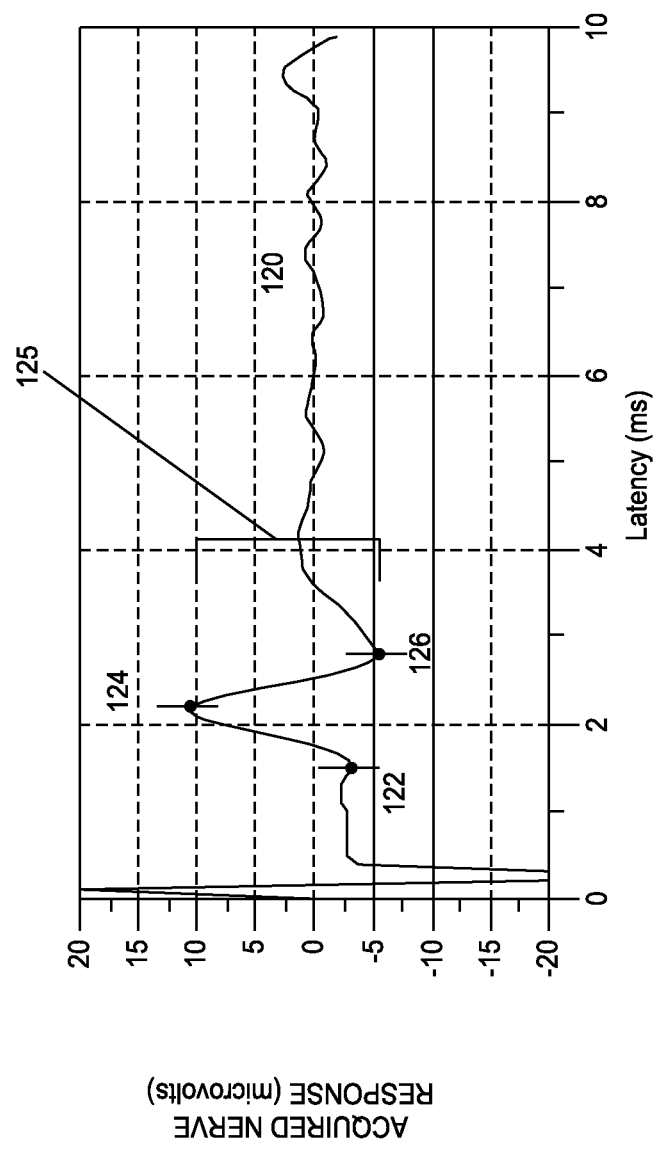
FIG. 10 is an example of an algorithmic analysis of a sural nerve response.
Figure 11:
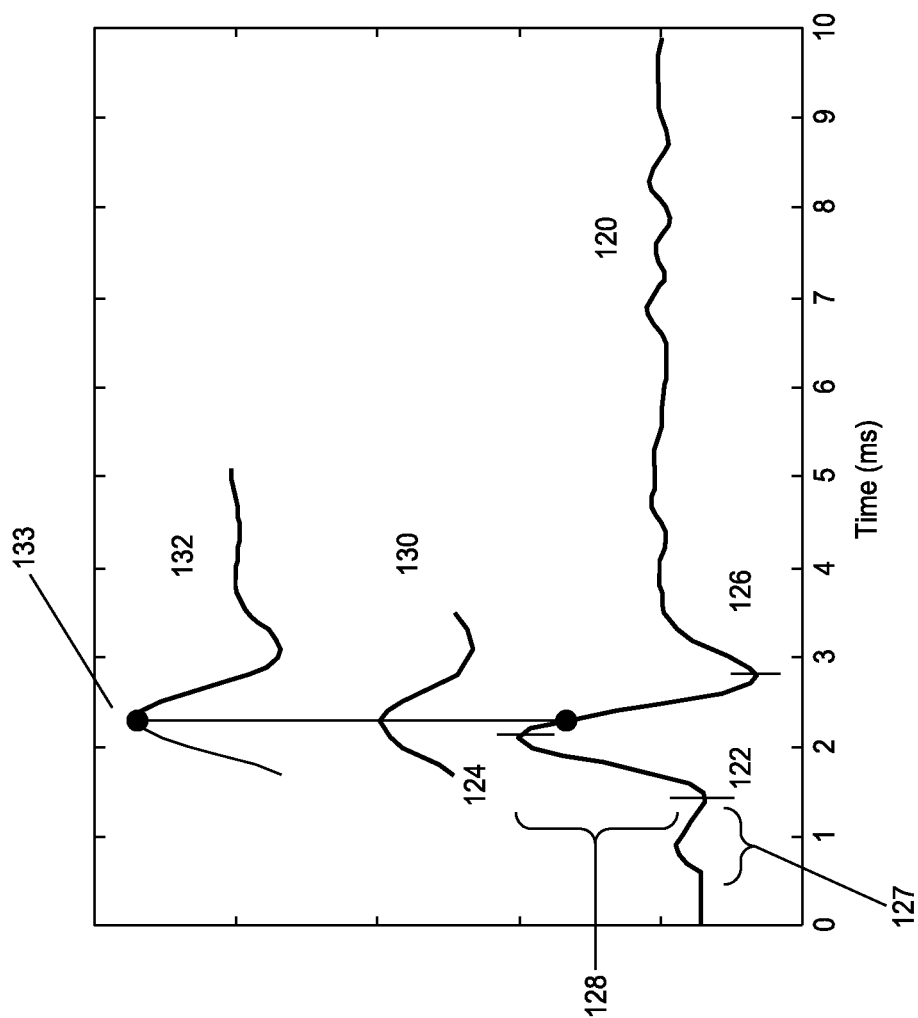
FIG. 11 is an example of how to determine sural nerve response waveform features.

STEP 5. FIG. 10 shows an example of an averaged sural nerve response 120 obtained by device 1. In the preferred embodiment (function block 174), device 1 determines three key waveform features: the nerve response onset 122, the response negative peak 124, and the response positive peak 126. These nerve response features are determined by a signal processing algorithm. The preferred embodiment of this signal processing algorithm is demonstrated through an example waveform shown in FIG. 11. Waveform 120 is a result of averaging one or more sural nerve responses. A generic sural nerve response template 130 is also constructed from a collection of waveforms acquired from multiple test subjects under the same data acquisition conditions (such as filter bandwidth and sampling frequency). As template 130 is slid from left-to-right (denoting a shift in time), a correlation between the shifted template and the averaged waveform 120 at different time shifts can be constructed as the correlation 132. In the preferred embodiment, the correlation is implemented as a sum of the products of the averaged waveform and the shifted template, normalized by the square root of the product of the energy in the averaged waveform 120 and the template 130. However, other forms of correlations may also be used if desired. The algorithm first determines the time 133 at which maximum correlation between the averaged response 120 and a fixed generic sural nerve response template 130 is achieved. The local maximum value of the averaged sural nerve response 120 closest to the correlation peak at time 133 is identified as the negative peak 124 of the sural response. The positive peak 126 of the sural response is the subsequent local minimum of waveform 120 and is identified by searching a pre-defined window that follows the negative peak 124. Onset 122 is preferably determined by a combination of two methods: curvature and two-line fit. The curvature method identifies the maximum curvature point of the averaged sural nerve response 120 preceding the negative peak 124. The two-line fit method searches for the best common point of two lines that approximate the baseline region 127 and the initial rising edge 128 of average sural nerve waveform 120.

Of course, it should also be appreciated that other techniques well known in the art may be used to determine the nerve response onset 122, the response negative peak 124 and the response positive peak 126.

Once device 1 determines the nerve response onset 122, the response negative peak 124, and the response positive peak 126, the device uses this information to determine (i) conduction velocity (CV), in meters per second, which is calculated as CV=(92.2/Onset), and (ii) the amplitude 125, in microvolts, which is calculated as the difference in amplitude between the negative peak 124 and positive peak 126. In a preferred embodiment of the present invention (function block 176), the CV is adjusted to compensate for the well known effect of temperature on conduction velocity before the CV and amplitude is displayed on LCD 26 (function block 178 in FIG. 12). More particularly, during the nerve conduction test, the skin surface temperature of the patient is measured by infrared thermometer 14 (FIG. 3)—preferably one measurement is made with each stimulation. The overall temperature is defined as the median of the individual temperatures. If the median temperature is below 23 degrees C., then an error message is reported to the user and no nerve conduction results are displayed. If the median temperature is 30 degrees C. or greater, then no temperature compensation is performed. For temperatures between 23 and 29.5 degrees C., the CV is corrected according to the following equation:

$$CV_{Displayed} = CV_{Calculated} Q_{10}^{(\Delta T/10)}$$

where $Q_{10}$ is a temperature coefficient and $\Delta T$ is the difference in temperature between 30 degrees C. and the median temperature. The preferred value for $Q_{10}$ is 1.5 based on published scientific studies.

Other Applications

Another application of the present invention is to detect alternative conductive path(s) on the surface of the skin in a transcutaneous electrical nerve stimulator (TENS). Although traditionally TENS devices do not record the response of the tissue being stimulated, an array of recording electrodes can be added together with data acquisition components similar to those components 100, 101, 102, 104 and 106 (FIG. 8) to provide a measurement of the stimulus artifact size. Alternative conductive path(s) on the skin surface could be caused by residual gel left on the skin from previous application of TENS therapy. If the skin is not properly cleaned, the residual gel may form an alternative conductive path between the cathode and anode stimulator electrodes. As with nerve conduction testing, the alternative conductive path in TENS therapy reduces the amount of stimulation current that flows into the tissue, thereby compromising the therapeutic efficacy of the TENS therapy.

Modifications

It should also be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A device for measuring sural nerve conduction velocity and amplitude, the device comprising:
   a housing;
   a stimulation means mounted to the housing for electrically stimulating a human sural nerve;
   a biosensor releasably mounted to the housing, the biosensor comprising a plurality of electrodes for detecting a sural nerve response evoked by the stimulation means;
   an acquisition means mounted to the housing and electrically connected to the biosensor for electrically acquiring the sural nerve response detected by the biosensor;
   a detection means mounted to the housing and electrically connected to the stimulation means and the acquisition means for detecting shorting or shunt of a stimulation current on a skin surface;
   a processing means mounted to the housing and electrically connected to the acquisition means for digitizing, processing and storing the acquired sural nerve response;
   a calculation means mounted to the housing and electrically connected to the processing means for calculating the conduction velocity and amplitude of the processed sural nerve response; and
   a display means mounted to the housing for displaying the sural nerve conduction velocity and amplitude;
   wherein the stimulation means and the biosensor are designed to be placed on a patient's anatomy, in the vicinity of the human sural nerve, by manipulating the housing;
   and further wherein the detection means utilizes a time constant of a decaying rate of a stimulus artifact recorded by the acquisition means to determine the likelihood of shorting or shunt of the stimulation current on the skin surface.

2. A device according to claim 1 wherein the detection means further utilizes a size of the stimulus artifact recorded by the acquisition means to determine the likelihood of shorting or shunt of the stimulation current on the skin surface.

3. A device according to claim 1 wherein the stimulation means comprises an anode probe and a cathode probe, and further wherein the detection means further utilizes a voltage difference between the anode probe and the cathode probe of the stimulation means to determine the likelihood of shorting or shunt of the stimulation current on the skin surface.

4. A device according to claim 1 wherein the stimulation means comprises an anode probe and a cathode probe, and further wherein the detection means utilizes a combination of a voltage difference between the anode probe and the cathode probe of the stimulation means and a size and the decaying rate of the stimulus artifact recorded by the acquisition means to determine the likelihood of shorting or shunt of the stimulation current on the skin surface.

5. A device according to claim 1 wherein the display means further displays an error message if the detection means determines that there is a shorting or shunt of the stimulation current on the skin surface.

6. A device for measuring sural nerve conduction velocity and amplitude, the device comprising:
   a housing;
   a stimulation means mounted to the housing for electrically stimulating a human sural nerve;
   a biosensor releasably mounted to the housing, the biosensor comprising a plurality of electrodes for detecting a sural nerve response evoked by the stimulation means;
   an acquisition means mounted to the housing and electrically connected to the biosensor for electrically acquiring the sural nerve response detected by the biosensor;
   a detection means mounted to the housing and electrically connected to the stimulation means and the acquisition means for detecting shorting or shunt of a stimulation current on a skin surface;
   a processing means mounted to the housing and electrically connected to the acquisition means for digitizing, processing and storing the acquired sural nerve response;
   a calculation means mounted to the housing and electrically connected to the processing means for calculating the conduction velocity and amplitude of the processed sural nerve response; and
   a display means mounted to the housing for displaying the sural nerve conduction velocity and amplitude;
   wherein the stimulation means and the biosensor are designed to be placed on a patient's anatomy, in the vicinity of the human sural nerve, by manipulating the housing;
   wherein the stimulation means comprises an anode probe and a cathode probe, and further wherein the detection means utilizes a combination of a voltage difference between the anode probe and the cathode probe of the stimulation means and a size and a decaying rate of a stimulus artifact recorded by the acquisition means to determine the likelihood of shorting or shunt of the stimulation current on the skin surface.

7. A device according to claim 6 wherein the detection means further utilizes a time constant of the decaying rate of the stimulus artifact recorded by the acquisition means to determine the likelihood of shorting or shunt of the stimulation current on the skin surface.

8. A device according to claim 6 wherein the display means further displays an error message if the detection means determines that there is a shorting or shunt of the stimulation current on the skin surface.

* * * * *